(12) United States Patent
Mintz et al.

(10) Patent No.: US 8,350,223 B2
(45) Date of Patent: Jan. 8, 2013

(54) QUANTUM DOT BASED RADIATION SOURCE AND RADIOMETRIC CALIBRATOR USING THE SAME

(75) Inventors: Nathan M. Mintz, Redondo Beach, CA (US); Kalin Spariosu, Thousand Oaks, CA (US)

(73) Assignee: Raytheon Company, Waltham, MA (US)

( * ) Notice: Subject to any disclaimer, the term of this patent is extended or adjusted under 35 U.S.C. 154(b) by 472 days.

(21) Appl. No.: 12/533,679

(22) Filed: Jul. 31, 2009

(65) Prior Publication Data

US 2011/0024612 A1 Feb. 3, 2011

(51) Int. Cl.
*G01D 18/00* (2006.01)

(52) U.S. Cl. ............... 250/365; 250/252.1; 250/552

(58) Field of Classification Search ............ 250/228, 250/365, 252.1, 552
See application file for complete search history.

(56) References Cited

U.S. PATENT DOCUMENTS

| | | | |
|---|---|---|---|
| 5,505,928 A | 4/1996 | Alivisatos et al. | |
| 6,178,865 B1 | 1/2001 | Roberts | |
| 6,322,901 B1 | 11/2001 | Bawendi et al. | |
| 6,338,292 B1 | 1/2002 | Reynolds et al. | |
| 6,344,272 B1 | 2/2002 | Oldenburg et al. | |
| 6,501,091 B1 | 12/2002 | Bawendi et al. | |
| 7,482,608 B2 * | 1/2009 | Zanrosso et al. | 250/493.1 |
| 2003/0044114 A1 * | 3/2003 | Pelka | 385/31 |
| 2004/0145289 A1 | 7/2004 | Ouderkirk et al. | |
| 2006/0068154 A1 | 3/2006 | Parce et al. | |
| 2006/0115917 A1 * | 6/2006 | Linden | 438/46 |
| 2006/0214903 A1 * | 9/2006 | Kurosaka | 345/102 |
| 2006/0237636 A1 | 10/2006 | Lyons et al. | |
| 2007/0034774 A1 | 2/2007 | Blake | |
| 2007/0242713 A1 | 10/2007 | Spariosu et al. | |
| 2009/0296368 A1 * | 12/2009 | Ramer | 362/84 |
| 2009/0320561 A1 * | 12/2009 | Fritz et al. | 73/24.02 |

FOREIGN PATENT DOCUMENTS

| | | |
|---|---|---|
| DE | 10 2004 047593 A2 | 4/2006 |
| EP | 1 696 224 A2 | 8/2006 |
| EP | 1 916 719 A2 | 4/2008 |
| WO | 2004068597 A2 | 8/2004 |
| WO | 2009/002512 A1 | 12/2008 |

OTHER PUBLICATIONS

J. Muller, et al. "Monitoring surface charge migration in the spectral dynamics of single CdSe/CdS nanodot/nanorod heterostructures," Physical Review, The American Physical Society, 2005, B 72, pp. 205339-1 to 205339-12.

Robert M. Kraus, et al., "Interplay between Auger and Ionization Processes in Nanocrystal Quantum Dots," The Journal of Physical Chemistry B Letters, 2005, 109, published on the Web Sep. 14, 2005, pp. 18214-18217.

(Continued)

*Primary Examiner* — David Porta
*Assistant Examiner* — Djura Malevic
(74) *Attorney, Agent, or Firm* — Lando & Anastasi, LLP (57) ABSTRACT

In one embodiment, a quantum dot based radiation source includes a housing having a wall defining a cavity therein, a plurality of quantum dots disposed on an inner surface of the wall of the housing, and a radiation excitation source in optical communication with the housing and configured to output radiation to excite the plurality of quantum dots to emit radiation in a desired wavelength range. The quantum dot based radiation source can be used in a calibration system or calibrator, for example to calibrate a detector.

20 Claims, 8 Drawing Sheets

OTHER PUBLICATIONS

R.A.M. Hikmet, et al., "Study of conduction mechanism and electroluminescence in CdSe/ZnS quantum dot composites," Journal of Applied Physics, vol. 93, No. 6, Mar. 15, 2003, pp. 3509-3514.

K. I. Rusakov, et al., "Control of Efficiency of Photon Energy Up-Conversion in CdSe/ZnS Quantum Dots," Optics and Spectroscopy, vol. 94, No. 6, 2003, pp. 859-863.

H. Borchert, et al., "High resolution photoemission study of CdSe and CdSe/ZnS core-shall nanocrystals," Journal of Chemical Physics, vol. 119, No. 3, Jul. 15, 2003, pp. 1800-1807.

William E. Buhro, et al., "Semiconductor Nanocrystals: Shape matters," Nature Materials, Nature Publishing Group, vol. 2, Mar. 2003, pp. 138-139.

None, "Sizing Curve of CdSe Nanocrystals," chart, NN-Labs, LLC, http://www.nn-labs.com/cdsesizintcurve.html, downloaded Dec. 12, 2008.

L. E. Brus, et al., "Nanocrystals and nano-optics," Phil. Trans., R. Soc. Lond., A, vol. 353, 1995, pp. 313-321.

Steve V. Kershaw, et al., Development of IR-Emitting Colloidal II-VI Quantum-Dot Materials, IEEE Journal of Selected Topics in Quantum Electronics, vol. 6, No. 3, May/Jun. 2000, pp. 534-543.

EPA No. 10164071.2 filed May 27, 2010, European Search Report dated Dec. 6, 2010 (6 pages).

\* cited by examiner

FIG. 1

FIG. 2
(BACKGROUND)

QUANTUM DOT BASED RADIATION SOURCE AND RADIOMETRIC CALIBRATOR USING THE SAME

BACKGROUND

This disclosure pertains to quantum dots, and particularly to a quantum dot based radiation source, a radiometric calibrator using the quantum dot radiation source, and a method of calibrating a detector using the quantum dot based radiation source.

Radiometric calibration is utilized to associate or link intensities measured by a sensor or detector (such as intensities measured by each pixel of a charge coupled device (CCD)) to a physical parameter. For example, radiometric calibration allows comparison of wavelength spectral intensities from different radiation sources. Radiometric calibration may be needed as the photon flux distribution in the unprocessed detected wavelength spectrum can be different from the photons flux distribution in the wavelength spectrum that is emitted by the observed object or source of radiation. This can be due to the fact that the photons detected by the sensor or detector (e.g., CCD) traversed several filters, such as the atmosphere, which can act as filter in certain regions of the wavelength spectrum, as well as filtering devices in the detector. Furthermore, radiometric calibration may be needed due to the fact that the detector or sensor quantum efficiency is not flat across the detected wavelength spectrum.

As a result, some degree of radiometric calibration may be needed by electro-optical instruments, such as electro-optical instruments used for remote sensing (e.g., space-based remote sensing instruments) to establish a relationship or link between the signal output by the instrument and the photon flux emitted by the object under study. For example, radiometric calibration may be used to know how a pixel's "dark number" correlates to a fixed unit of illumination (W/cm$^2$ or photons/cm$^2$-s). Furthermore, radiometric calibration can also provide meaningful comparison of different observed phenomena.

Current radiometric calibration is performed primarily by using a bright filament-based lamp as a radiation source. For example, in order to simulate the blackbody output of the sun, the filament or filaments in the lamp are operated at relatively high temperatures (e.g., approximately 3500 K or more). This creates a number of problems in terms of heat dissipation, power consumption, volume and reliability. Furthermore, the use of a lamp wherein the filament is operated at a relatively high temperature can pose additional challenges. Indeed, the lamp must be mechanically manipulated with an aperture wheel to achieve a desired dynamic range. In addition, the radiation output of the lamp can vary (e.g., degrade) over time due to changing electrical loads or due to changes in filament characteristics. Also, this type of radiation source is generally not stable over its useful life span.

Instead of filament-based lamps, light emitting diodes (LEDs) have also been used for radiometric calibrations. LEDs are generally more stable than filament based lamps. However, LEDs emit in narrow wavelength ranges and, as a result, can only cover a limited portion of the radiation spectrum.

Other light sources used for radiometric calibration include the use of solar diffusers which usually require checks by other sources (ground images). However, the solar diffusers degrade over life due to material degradation, contamination or mechanical problems. The use of solar diffusers for calibration include calibrating ex-situ by looking at features on the ground that have a known reflectivity. For example, the instrument stares at a patch of snow on the earth. However, these methods have limitations, since the reflectivity of the material (e.g., snow on the ground surface) can change over time and thus affect the reflected spectrum.

This disclosure addresses various issues relating to the above and other issues with conventional approaches.

SUMMARY

An embodiment of this disclosure provides a quantum dot based radiation source comprising a housing having a wall defining a cavity therein, a plurality of quantum dots disposed on an inner surface of the wall of the housing; and a radiation excitation source in optical communication with the housing and configured to output radiation to excite the plurality of quantum dots to emit radiation in a desired wavelength range.

Another embodiment of this disclosure provides a calibration system or calibrator comprising a quantum dot based radiation source and an integrating sphere configured to receive radiation emitted by the quantum dot based radiation source. The quantum dot based radiation source includes a housing having a wall defining a cavity therein, a plurality of quantum dots disposed on an inner surface of the wall of the housing, and a radiation excitation source in optical communication with the housing and configured to output radiation to excite the plurality of quantum dots to emit radiation in a desired wavelength range.

Yet another embodiment of this disclosure provides a method of calibrating a radiation detector. The method comprises exciting a plurality of quantum dots with a first radiation so that the quantum dots emit a second radiation in a desired wavelength range, the quantum dots being disposed on an inner surface of a wall of a housing defining a cavity therein; outputting the second radiation through an output port in the housing; and guiding the second radiation towards the radiation detector to calibrate the detector.

These and other features and characteristics of this disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. As used in the specification and in the claims, the singular form of "a", "an", and "the" include plural referents unless the context clearly dictates otherwise.

DETAILED DESCRIPTION

Figure 1:
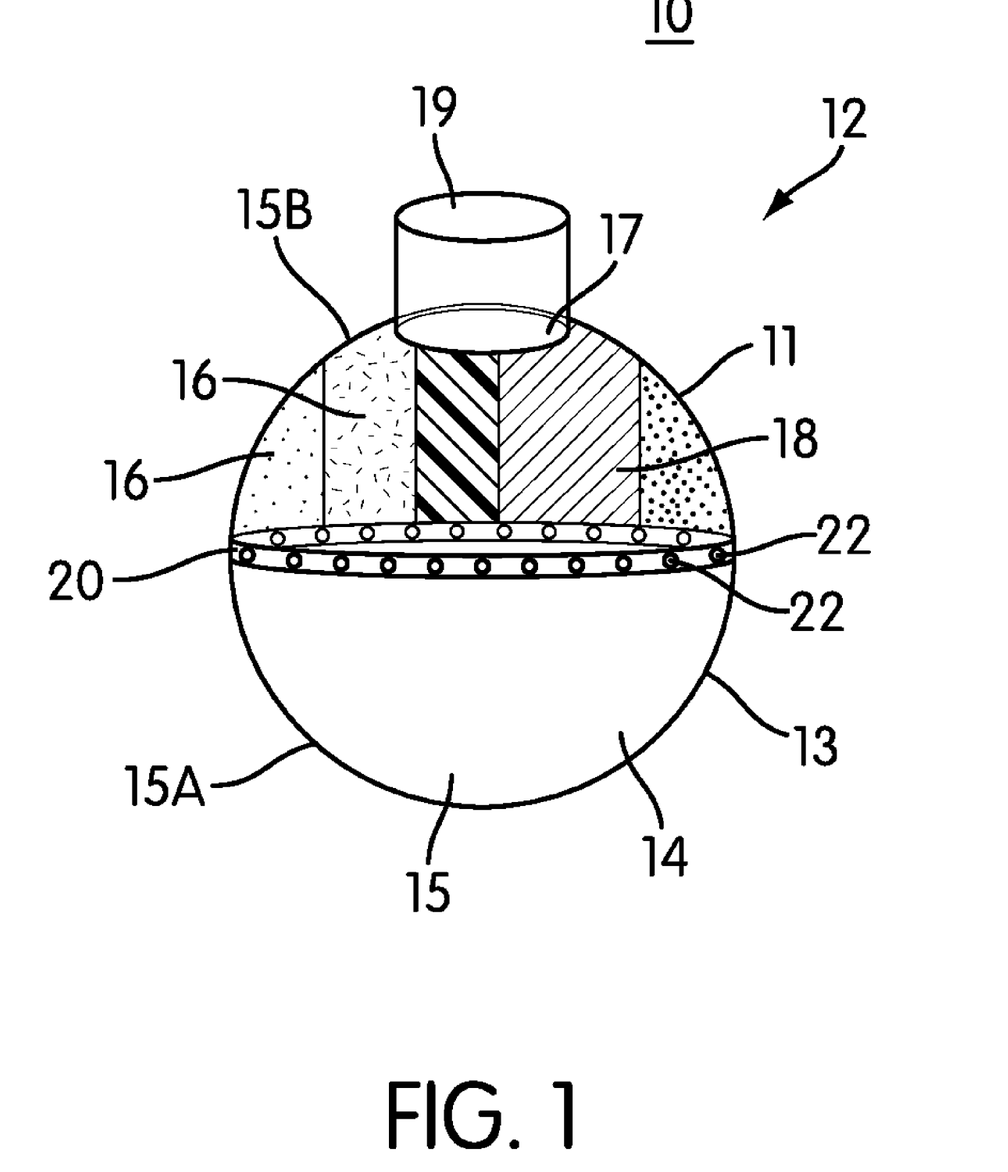
FIG. 1 is a schematic representation of a quantum dot based radiation source, according to an embodiment.

FIG. 1 is a schematic representation of a quantum dot based radiation source, according to an embodiment. Quantum dot based radiation source 10 includes integrating sphere 12. Integrating sphere 12 includes housing 11 having wall 13 forming hollow cavity 14. Inner surface 15 of wall 13 of integrating sphere 12 is coated with radiation diffusing reflective coating, such as SPECTRALON™ or SPECTRAFLECT™ coatings manufactured by Labsphere, Inc. The shape of cavity 14 is commonly spherical, hence the name of "integrating sphere". However, as it can be appreciated, housing 11 defining cavity 14 can have other shapes such as dodecahedron, icosidodecahedron, icosahedron, or the like. In general, an integrating sphere is used for its diffusing effect. Radiation rays incident on any point on the inner surface of the wall of the integrating sphere is distributed equally to all other points by multiple scattering reflections. As a result, the effects of the original direction of such light are minimized. Hence, an integrating sphere may be seen as a diffuser which preserves power but destroys spatial information.

In one embodiment, portion 15A of inner surface 15 of wall 13 (e.g., about one half of inner surface 15 or one hemisphere) is coated with the radiation reflective coating while another portion 15B of inner surface 15 of wall 13 (e.g., the other half of total inner surface 15 or opposite hemisphere) is not coated with the radiation reflective coating. Instead, a plurality of panels 16 coated with quantum dots 18 are provided on portion 15B of inner surface 15 of wall 13.

Quantum dot based radiation source 10 further includes excitation radiation source 20. Excitation radiation source 20 is used to excite quantum dots 18 to emit a photon (one or more photons). In one embodiment, excitation radiation source 20 comprises a plurality of light emitting diodes (LEDs) 22. However, as it can be appreciated any other type of source can be used. Excitation radiation source 20 (e.g., LEDs 22) is in optical communication with housing 11. In one embodiment, LEDs 22 can be disposed spaced apart around the "equator" of integrating sphere 22. However, as it can be appreciated LEDs 22 can be arranged in housing 11 of integrating sphere 22 in any desired location and/or configuration. For example, LEDs 22 can be provided at one spot of housing 11. LEDs 22 can be selected according to their radiation power output and/or their spectral output. For example, LEDs 22 can be selected from LEDs that emit in the ultraviolet (UV) spectrum such as UV LEDs made by Phoseon Technology Corporation. Alternatively, the excitation radiation source 20 (e.g., LEDs 22) can be provided remote from the housing 11 and optical waveguides (e.g. optical fibers) can be used to guide the radiation emitted by the excitation radiation source 20 to the quantum dots 18.

Figure 2:
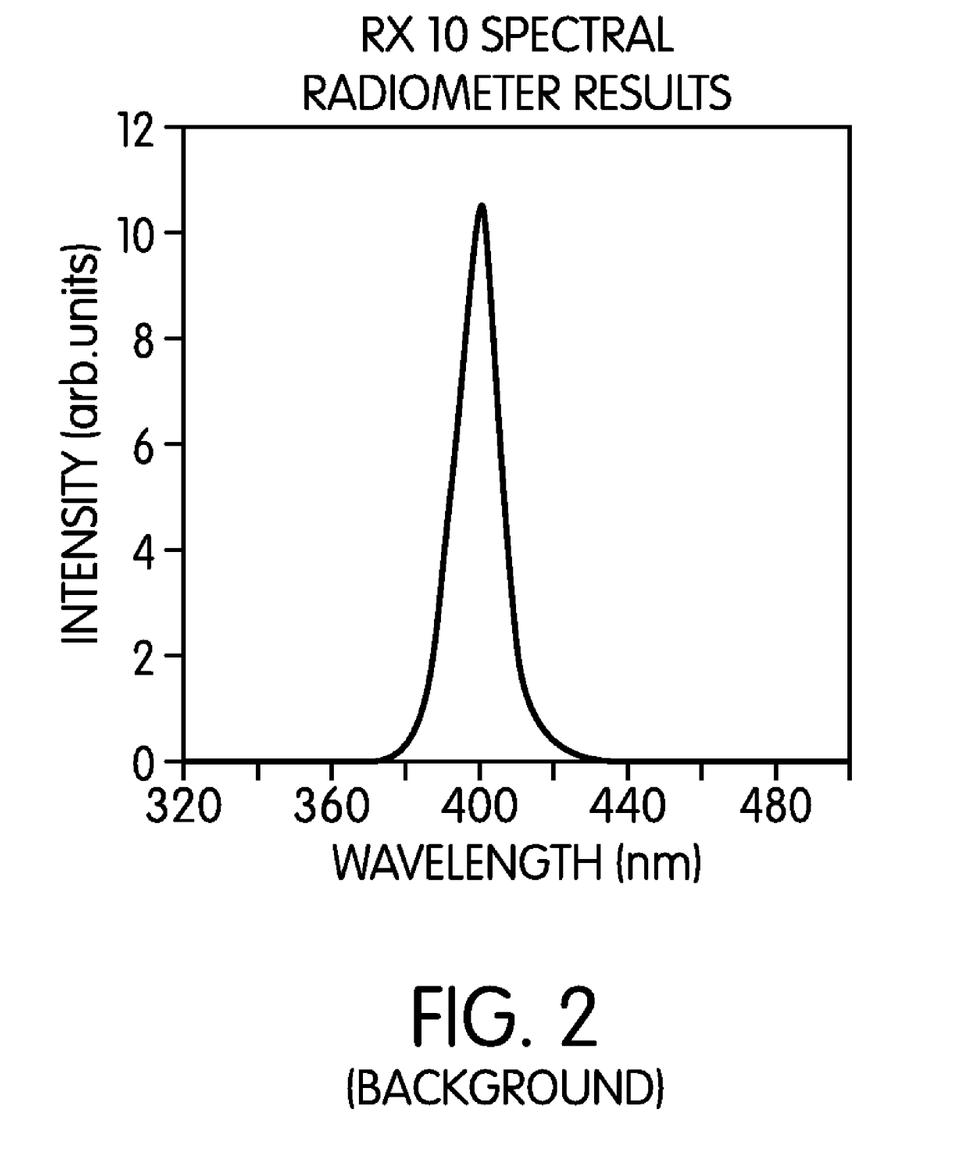
FIG. 2 shows an example of the radiation spectrum output by a UV LED.

FIG. 2 shows an example of the spectrum of radiation output by a UV LED. The UV LED can provide a stable intensity output over the operation lifetime of the UV LED which can be 15000 hours or more. LEDs 22 can be selected to emit in a same range of wavelengths or different ranges of wavelengths. For example, in one embodiment, some of LEDs 22 can be selected to emit in one ultraviolet wavelength range while other LEDs 22 can be selected to emit in another ultraviolet wavelength range or in the visible wavelength range.

Radiation emitted by excitation radiation source 20 (e.g., light emitted by LEDs 22) can undergo multiple reflections by the radiation reflective coating on inner surface portion 15A. The reflected excitation radiation is absorbed by quantum dots 18 disposed on substrate panels 16. The quantum dots in turn emit radiation at a wavelength equal or longer than the wavelength of excitation radiation source 20 (e.g., LEDs 22). In other words, excitation radiation source 20 has a wavelength shorter than or equal to the wavelength emitted by quantum dots 18. The radiation emitted by the quantum dots also undergoes multiple reflections by the radiation reflective coating within cavity 14.

Exit or output port 17 is provided in wall 13 to allow radiation that is emitted by the quantum dots and reflected and diffused by the coating on inner surface 15 to exit through exit port 17. Tube 19 may be provided to guide the light output through output port 17.

Figure 3:
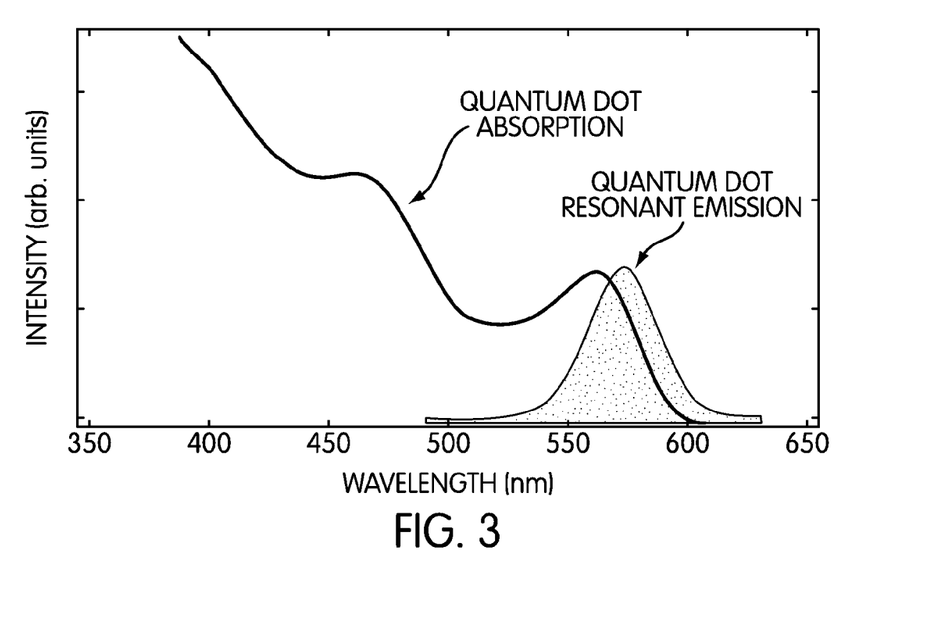
FIG. 3 depicts a theoretical broad range absorption spectrum of the quantum dots along with the narrow resonant emission characteristic of quantum dots.

Upon absorbing a photon, quantum dots 18 can reemit a photon (or under certain circumstances multiple photons) at the characteristic wavelength of the quantum dots. The characteristic wavelength of quantum dots 18 can be tuned by selecting a size of quantum dots 18. FIG. 3 depicts a theoretical broad range absorption spectrum of quantum dots 18 along with the narrow resonant emission characteristic of quantum dots 18. Therefore, quantum dots 18 act as a frequency downconverter for the radiation emitted by excitation radiation source 20 (e.g., LEDs 22) into specific frequency ranges. Because each quantum dot has a certain defined carrier lifetime, each quantum dot has a defined saturation rate which results in the quantum dot having a defined unit of emitted radiation intensity.

Figure 4:
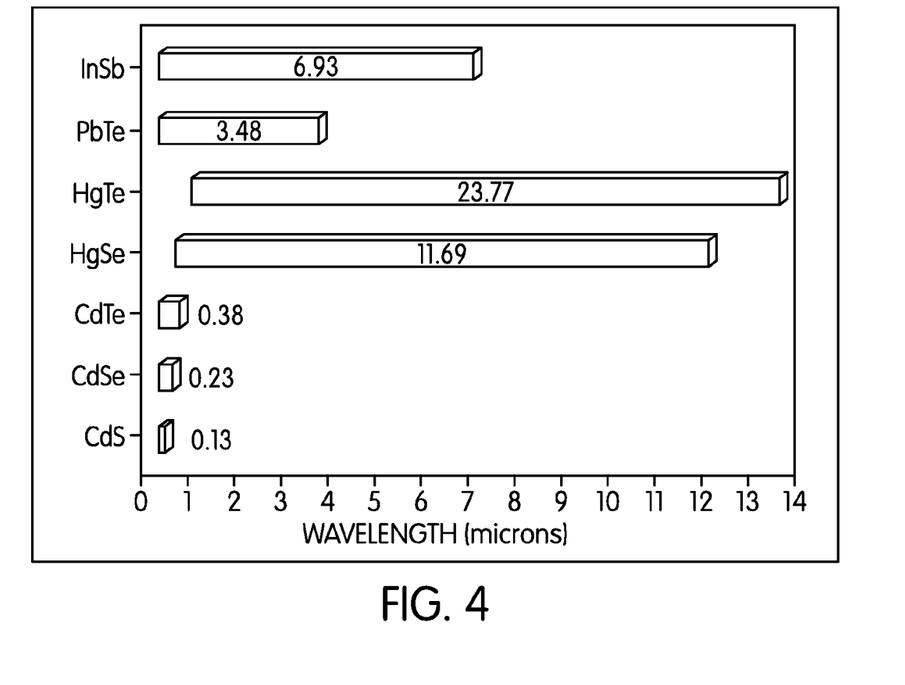
FIG. 4 shows a wavelength emission range of various quantum dot materials depending upon the size of the quantum dots.

FIG. 4 shows the emission range of various quantum dot materials (e.g., InSb, PbTe, HgTe, HgSe, CdTe, CdSe and CdS) depending upon the size of the quantum dots. The right end of each bar represents the emission peak of the corresponding bulk material. The left end of each bar represents the resonant emission peak for a 3 nm size quantum dot corresponding to the same bulk material. By using one or more of the quantum dot materials listed above, a specific emission wavelength range can be covered. For example, a specific mixture of quantum dots as well as the size of the quantum dots can be selected so as to cover a desired emission wavelength range. Alternatively or in addition, other composite semiconductor materials such as lead tin telluride (PbSnTe) can also be used to make the quantum dots.

Furthermore, since each individual quantum dots has a defined emission intensity and wavelength band, a mixture of quantum dots can be made with ratios of different sizes and/or types of materials to produce a characteristic emission profile over a broad portion of the spectrum.

Figure 5:
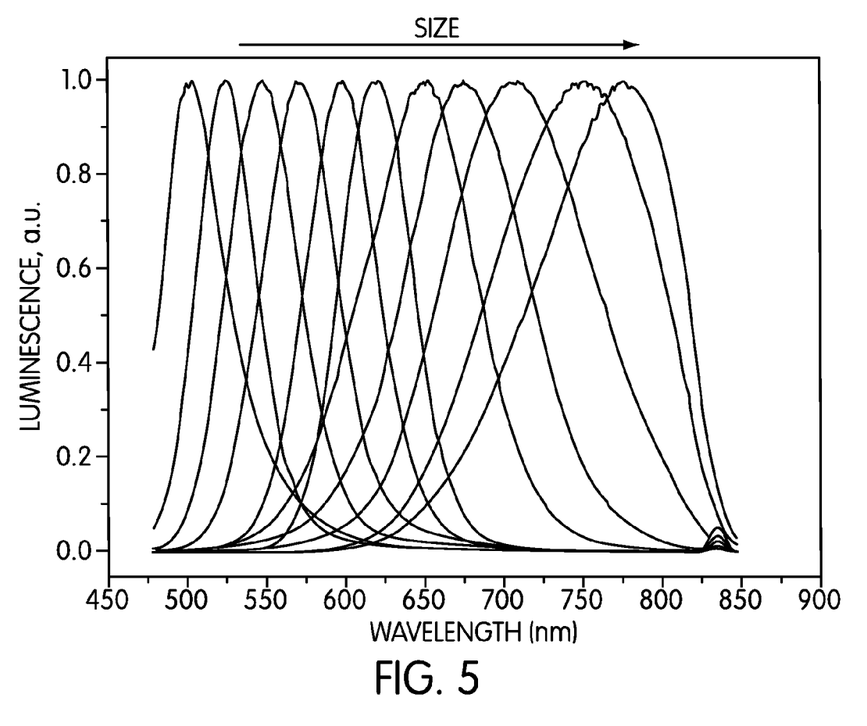
FIG. 5 is a plot of luminescence peaks of CdSe quantum dots as a function of wavelength for various sizes of the CdSe quantum dots.
Figure 6:
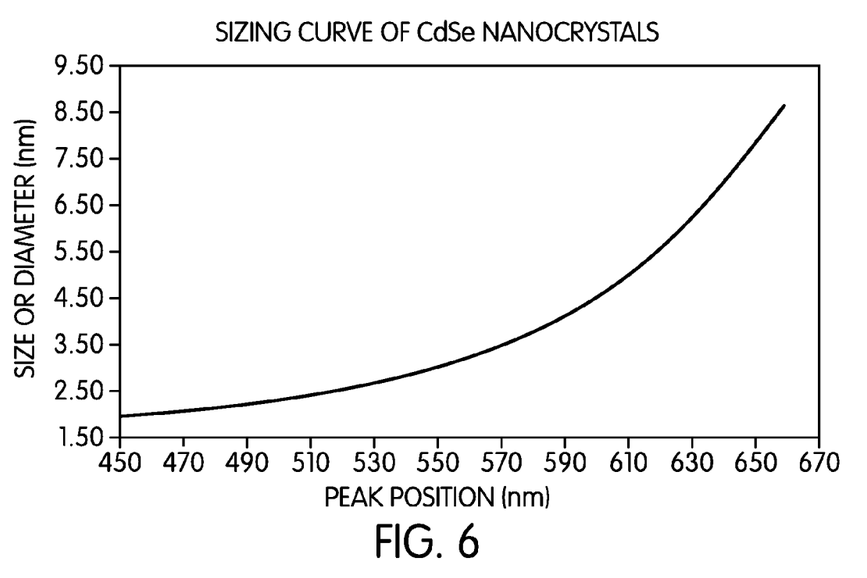
FIG. 6 is a plot showing the relationship between the wavelength of emitted radiation peak and the size (e.g., diameter) of the quantum dots.

For example, FIG. 5 shows a plot of luminescence peaks of CdSe quantum dots as a function of wavelength for various sizes of the CdSe quantum dots. As shown in FIG. 5, the larger the size of the quantum dots, the greater is the wavelength of the peak emitted light. FIG. 6 is a plot showing the relationship between the wavelength of emitted radiation peak and the size (e.g., diameter) of the quantum dots. As shown in FIG. 6, the wavelength of the emitted radiation peak increases with the increasing size (e.g., increasing diameter) of the quantum dots (e.g., CdSe nanocrystals).

A number of methods for producing quantum dots are known in the art. Any method of producing quantum dots which can emit in a desired range of wavelengths such as Visible (VIS) and IR including LWIR, MWIR and/or SWIR ranges, can be used herein. For example, colloidal methods can be used to synthesize quantum dots. The synthesis of colloidal quantum dots is based on a three component system composed of: precursors, organic surfactants, and solvents. When heating a reaction medium to a sufficiently high temperature, the precursors chemically transform into monomers. Once the monomers reach a high enough supersaturation level, the nanocrystal growth starts with a nucleation process. The temperature during the growth process is one of the factors in determining optimal conditions for the nanocrystal growth. The temperature is high enough to allow for rearrangement and annealing of atoms during the synthesis process while being low enough to promote crystal growth. Another factor that needs to be controlled during nanocrystal growth is the monomer concentration to achieve a homogenous quantum dot size.

In addition quantum dots can be encapsulated in a shell to achieve certain radiation emission characteristics. For example, in one embodiment, quantum dots can be produced according to a method disclosed in U.S. Pat. No. 6,322,901 to Bawendi et al., the entire contents of which are incorporated herein by reference. U.S. Pat. No. 6,322,901 discloses a method of overcoating quantum dots composed of CdS, CdSe or CdTe with ZnS, ZnSe. In another embodiment, quantum dots can be fabricated according to a method disclosed in U.S. Pat. No. 6,344,272 to Oldenburg et al., the entire contents of which are also incorporated herein by reference. However, other methods can be employed to produce desired quantum dots according to the application sought.

Panels 16 can be coated with different types of quantum dots 18. For example, one or more panels 16 can be coated with a first type of quantum dots, while one or more other panels 16 can be coated with a second type of quantum dots. For example, the first type and the second type of quantum dots can be quantum dots of different materials or chemical composition, or quantum dots having different dimensions, or both. By providing quantum dots of different materials and/or quantum dots of different dimensions, a specific emission wavelength range can be obtained.

Figure 7:
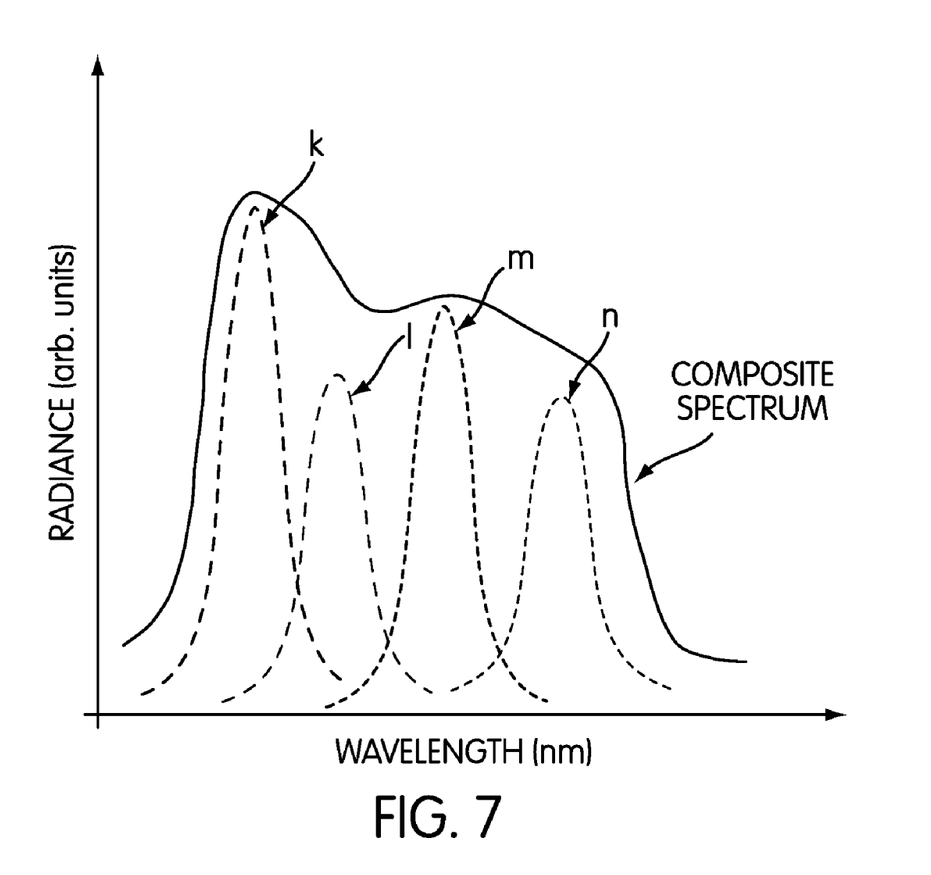
FIG. 7 shows a composite spectrum obtained by using various types of quantum dots, according to one embodiment.

FIG. 7 shows a composite spectrum obtained by using various types of quantum dots, according to one embodiment. Each type of quantum dots emits a distinctive radiation peak k, l, m and n. It is worth noting that although each type of quantum dots emits in a relative narrower range of wavelengths, by combining various types of quantum dots emitting in substantially separate or distinct wavelength ranges, the overall obtained emission wavelength range (composite spectrum) covers the wavelength ranges of k, l, m and n radiation peaks. As a result the combined spectrum is broader to cover a desired wavelength range. By type of quantum dots, it is meant quantum dots made from a certain material (or having a certain chemical composition) or quantum dots having a specific dimension or size, or both. For example, the radiation peak k is obtained using a first type of quantum dots having a chemical composition, a size, or both different from a chemical composition, a size, or both of a second type of quantum dots emitting radiation peak l.

Figure 8:
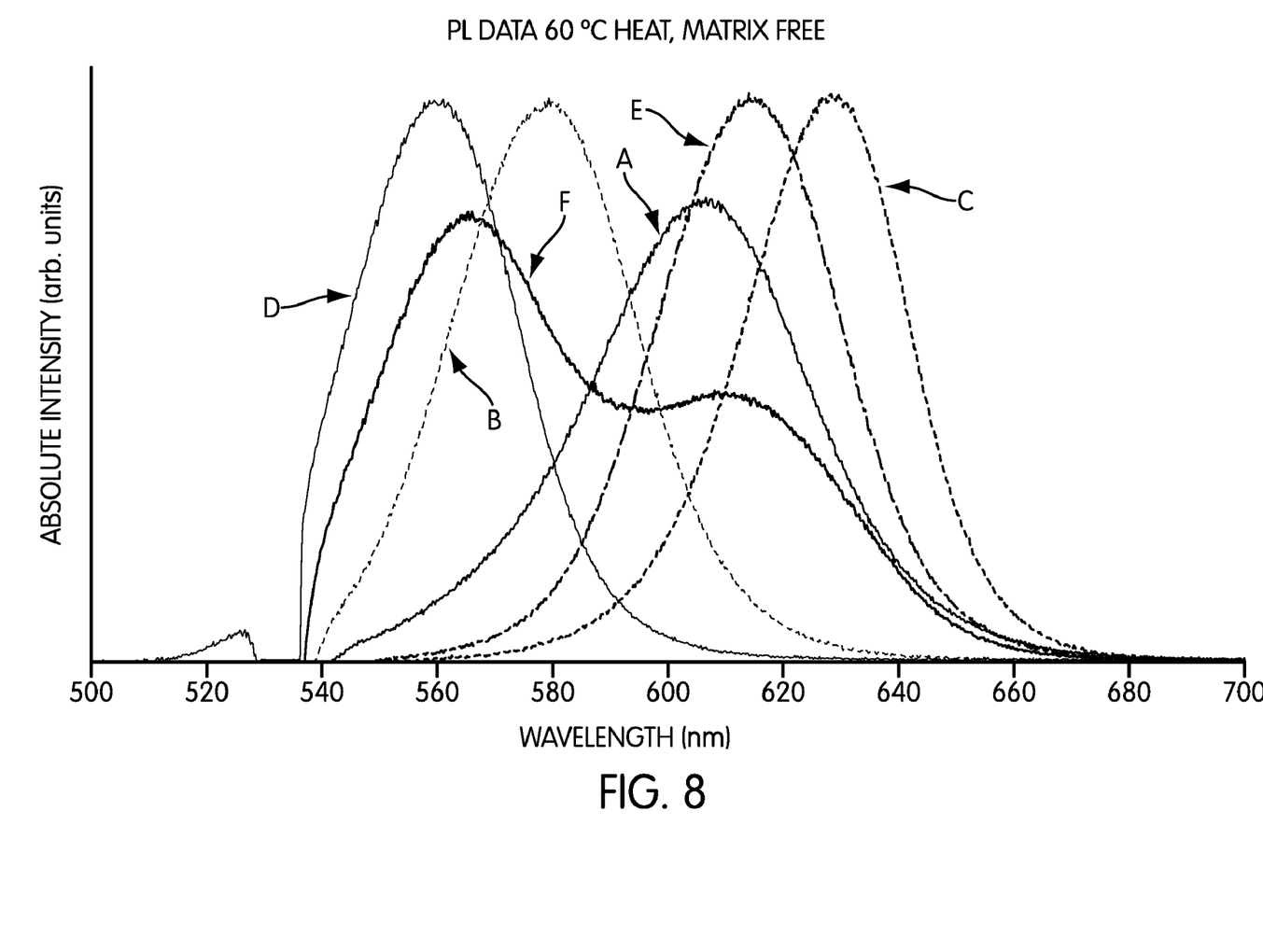
FIG. 8 shows emission spectra of various quantum dot types when excited with ultraviolet radiation, according to one embodiment.

FIG. 8 shows emission spectra of various quantum dot types when excited with ultraviolet radiation, according to one embodiment. These spectra are obtained by exciting the quantum dots with ultraviolet radiation while heating the quantum dot at about 60° C. In this embodiment, the quantum dots are not imbedded in a matrix such as a polymer matrix. The quantum dots are spread on a substrate and excited with ultraviolet radiation. As shown in FIG. 8, one type of quantum dots emits a peak of radiation (peak A) centered around about 600 nm, another type of quantum dots emits a peak of radiation (peak B) centered around about 580 nm, another type of quantum dots emits a peak of radiation (peak C) centered around about 630 nm, another type of quantum dots emits a peak of radiation (peak D) centered around about 560 nm, and another type of quantum dots emits a peak of radiation (peak E) centered around about 620 nm. In one embodiment, the above five types of quantum dots are spread as layers and stacked on a substrate. The stacked layers of quantum dots are then excited with ultraviolet radiation. The stacked layers of quantum dots emit a relatively broad spectrum of radiation (spectrum F) from about 540 nm to about 680 nm. This shows that a broad spectrum emitting radiation source can be created by using various types of quantum dots.

Figure 9:
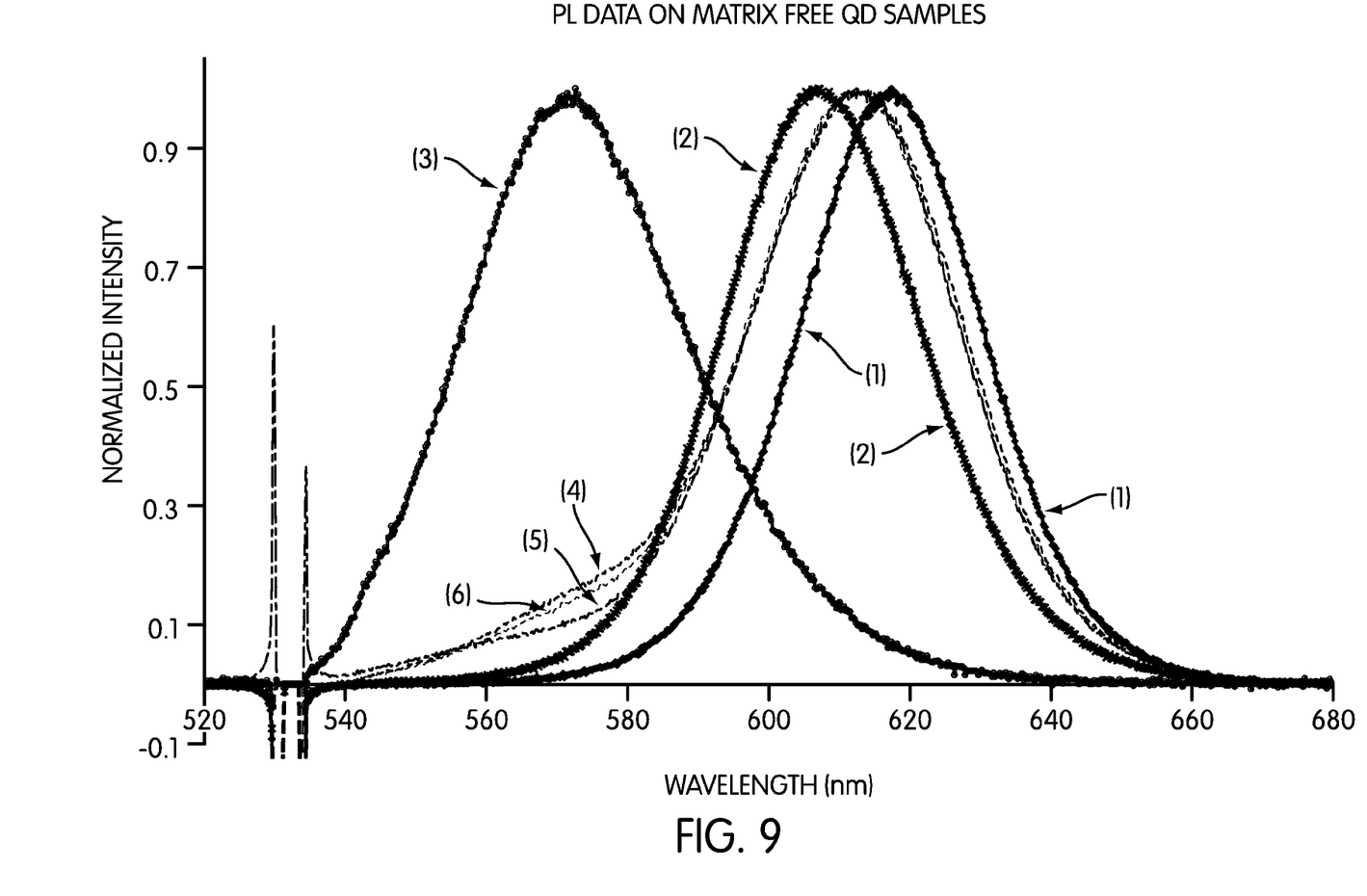
FIG. 9 shows emission spectra of various quantum dot types when excited with ultraviolet radiation, according to another embodiment.

FIG. 9 shows emission spectra of various quantum dot types when excited with ultraviolet radiation, according to another embodiment. These spectra are obtained by exciting the quantum dots with ultraviolet radiation without heating the quantum dots. In this embodiment, the quantum dots are also not imbedded in a matrix such as a polymer matrix. The quantum dots are spread on a substrate and excited with ultraviolet radiation. As shown in FIG. 9, one type of quantum dots emits peak (1) of radiation centered around about 620 nm, another type of quantum dots emits peak (2) of radiation centered around about 600 nm, and another type of quantum dots emits peak (3) of radiation centered around about 560 nm. In one embodiment, the above 3 types of quantum dots are spread as layers and stacked on a substrate. The stacked layers of quantum dots are then excited with ultraviolet radiation.

In one example, the type of quantum dots emitting the peak of radiation (3) is deposited first on the substrate, followed by the type of quantum dots emitting the peak of radiation (2), then the type of quantum dots emitting the peak of radiation (1) to obtain a stack of quantum dots emitting a peak of radiation (4) centered around about 620 nm when excited with ultraviolet radiation. In another example, the type of quantum dots emitting the peak of radiation (1) is deposited first on the substrate, followed by the type of quantum dots emitting the peak of radiation (2), then the type of quantum dots emitting the peak of radiation (3) to obtain a stack of quantum dots emitting a peak of radiation (6) centered around about 620 nm when excited with ultraviolet radiation. Hence, one can see that, in this embodiment, the emission peak of the obtained stack of quantum dot layers is independent of the arrangement of the quantum dots layers in the stack. Although, in the above embodiments the quantum dots are not imbedded in a polymer matrix, however, as it can be appreciated the quantum dots can also be imbedded in a polymer matrix.

In yet another example, instead of depositing the various types of quantum dots as stacked layers, the types of quantum dots emitting the various peak of radiation (1), (2) and (3) are mixed together to form a "cocktail" or mixture of quantum dots. The mixture of quantum dots is then excited with ultraviolet wavelength. The excited mixture of quantum dots emits a peak of radiation (5) centered around about 620 nm. The emission peak of radiation (5) obtained in the case of mixing the quantum dots and the emission peaks of radiation (4) and (6) obtained in the case of stacking the layers of the various types of quantum dots are substantially similar indicating that the resultant emission spectrum is independent from the relative position of the various types quantum dots.

In the above example, the selected quantum dots emit in the visible (VIS) wavelength range. However, as it can be appreciated, different types of quantum dots can be selected by selecting a specific material (or chemical composition) of the quantum dots and/or selecting a size of the quantum dots so that the selected quantum dots emit in any range including VIS (between about 400 nm and about 800 nm), SWIR (between about 1 μm and about 3 μm), MWIR (between about 3 μm and about 8 μm) and LWIR (between about 8 μm and about 12 μm). For example, a mixture of quantum dots can be selected so that the combined radiation emission spectrum of the quantum dots has a broad wavelength range to simulate the spectrum of sunlight.

Figure 10:
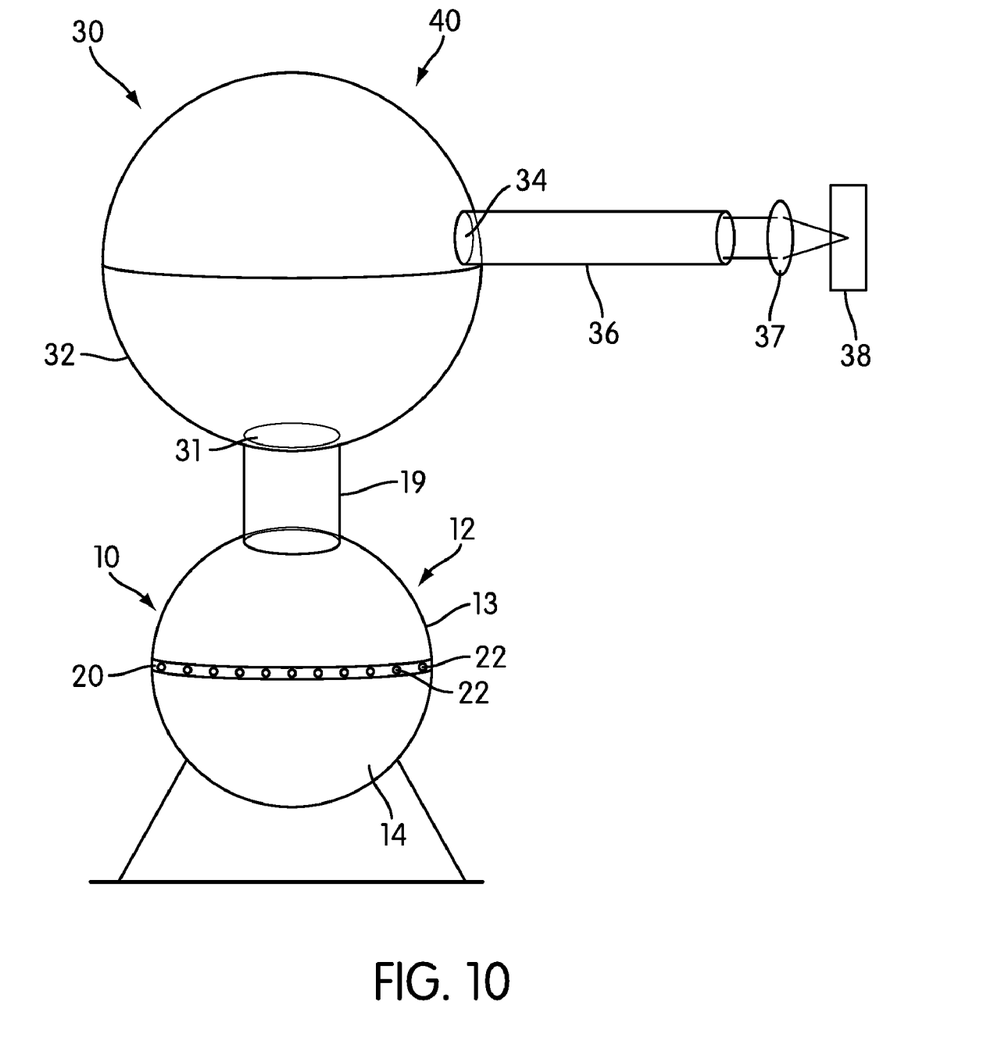
FIG. 10 shows a calibration system or calibrator using the quantum dot based radiation source shown in FIG. 1, for calibrating a detector, according to one embodiment.

FIG. 10 shows a calibration system or calibrator using quantum dot based radiation source 10 shown in FIG. 1 for calibrating a detector, according to an embodiment. Calibration system 40 comprises quantum dot based radiation source 10 and integrating sphere 30. Inlet port 31 of integrating sphere 30 is connected to quantum dot based radiation source 10 via tube 19. Integrating sphere 30 operates generally in the same manner as described above with respect to integrating sphere 12 of quantum dot based radiation source 10. Radiation generated by the quantum dots of quantum dot based radiation source 10 is guided through tube 19 into integrating sphere 30 where the radiation is further reflected and diffused by a coating on an inner surface of wall 32 of integrating sphere 30. The radiation diffused in integrating sphere 30 is output through output port 34 of integrating sphere 30. Waveguide 36 may be provided to guide the radiation output from integrating sphere 30 towards detector 38, e.g., a focal plane array (FPA). Optics 37 (e.g., a lens) can be used to focus the beam onto the FPA.

Using the radiation output by calibration system 40, detector 38 can be calibrated so as to establish a relationship or link between the signal output by the detector and the photon flux emitted by an object under study. Calibration system 40 can be used, for example, in calibrating the signal output by space based radiometric instruments, such as instrument using an FPA detector for remote sensing applications.

In remote sensing space based applications, a detector (e.g., FPA) can be, for example, configured to detect radiation with a sensitivity on the order of 100-200 photons in the SWIR wavelength, corresponding to a few picowatts to nanowatts in equivalent power. For example, if an object on a surface of the earth (e.g., a patch of snow reflecting sunlight) emits or reflects radiation, the radiation power P (in Watts) detected by a pixel in the FPA detector in space can be calculated by the following equation (1).

$$P = I \cdot s \cdot \frac{H}{f}, \quad (1)$$

where I is the intensity of the emitted or reflected light reaching the sensor from the object, s is the area of a pixel on the FPA detector, H is the altitude of the remote sensing instrument or the distance between the object and the FPA detector, and f is the focal length of the instrument's optics.

If one estimates that the intensity of the radiation emitted or reflected by the object is about 200 W/m² at the earth's surface, the intensity I of light reaching the detector can be calculated by taking into account the location of the instrument at an altitude H. Indeed, the radiation intensity drops off at a rate corresponding to the inverse square law. Hence, if one assumes that the remote sensing instrument is at an altitude H of about 400 km above the earth's surface, the intensity I of the light reaching the remote sensing instrument (detector) will correspond to approximately 2.5 nW/m². If the area of a pixel s is about 400 μm² (20 μm by 20 μm), and the focal length f is about 20 m, the obtained power P is about $2 \cdot 10^{-14}$ W.

The total field of regard (FOR) of the sensor or detector can be determined using the following equation (2), $$FOR = \left(l \cdot \frac{H}{f}\right)^2 N^2, \quad (2)$$

where N is the number of pixels along a dimension l in the focal plane, H is the altitude of the remote sensing instrument or the distance between the object and the detector, and f is the focal length of the instrument's optics.

Using the same inputs as in the above paragraphs, one can determine that the total field of regard of the sensor is about 160,000 m² (0.16 km²). The radiation power needed for calibrating the detector is the average power per pixel (determined using equation 1) multiplied by the field of regard. Hence, taking into account any attenuation from the optics, a power of a few nanowatts may be sufficient to calibrate the FPA detector with a million equally sized pixels. A power of a few microwatts net equivalent power can be output by the quantum dot based radiation source described in the above paragraphs, which is more than sufficient to serve as a calibration source.

Although the inventive concept has been described in detail for the purpose of illustration based on various embodiments, it is to be understood that such detail is solely for that purpose and that the inventive concept is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

Furthermore, since numerous modifications and changes will readily occur to those with skill in the art, it is not desired to limit the inventive concept to the exact construction and operation described herein. Accordingly, all suitable modifications and equivalents should be considered as falling within the spirit and scope of the present disclosure.

What we claim is:

1. A quantum dot based radiation source, comprising:

a housing having a wall defining a cavity therein;

a plurality of quantum dots disposed on a plurality of substrate panels disposed on a first portion of an inner surface of the wall; and a radiation excitation source in optical communication with the housing and configured to output first radiation to excite the plurality of quantum dots to emit second radiation in a desired wavelength range;

wherein a second portion of the inner wall of the housing is coated with a radiation reflective material selected to reflect the second radiation emitted by the plurality of quantum dots, the first portion of the inner surface of the wall is free of the radiation reflective material, and the first and second portions of the inner surface of the wall are mutually exclusive.

2. The radiation source of claim 1, wherein the second radiation emitted by the plurality of quantum dots is dependent upon a chemical composition of the plurality of quantum dots or a size of the plurality of quantum dots, or both.

3. The radiation source of claim 1, wherein the plurality of quantum dots comprise quantum dots of various sizes, or various chemical compositions, or both.

4. The radiation source of claim 1, wherein the plurality of quantum dots comprise a first type of quantum dots emitting radiation in a first wavelength range and a second type of quantum dots emitting radiation in a second wavelength range substantially distinct from the first wavelength range such that the second radiation emitted by the plurality of quantum dots has a wavelength spectrum that extends over the first and the second wavelength ranges.

5. The radiation source of claim 4, wherein the first type of quantum dots has either a chemical composition, a size, or both, different from a chemical composition or a size, or both of the second type of quantum dots.

6. The quantum dot based radiation source of claim 4, wherein the plurality of substrate panels includes a first panel and a second panel, wherein the first type of quantum dots are disposed on the first panel and the second type of quantum dots are disposed on the second panel.

7. The quantum dot based radiation source of claim 6, wherein the first wavelength range includes wavelengths that are longer than wavelengths in the second wavelength range, and wherein the first type of quantum dots are larger than the second type of quantum dots.

8. The quantum dot based radiation source of claim 4, wherein the first and second types of quantum dots are spread as layers and stacked on at least one of the plurality of substrate panels.

9. The radiation source of claim 1, wherein the first radiation has a shorter wavelength than a wavelength of the second radiation emitted by the quantum dots.

10. The radiation source of claim 9, wherein the first radiation output by the excitation radiation source comprises ultraviolet radiation.

11. The radiation source of claim 1, wherein the plurality of quantum dots are selected from the group consisting of InSb, PbTe, HgTe, CdTe, CdSe, CdS, and PbSnTe.

12. The radiation source of claim 1, wherein the radiation source includes an integrating sphere, wherein the housing is spherical.

13. The radiation source of claim 12, wherein the first and second portions of the inner surface of the wall of the housing are first and second hemispheres of the wall.

14. The radiation source of claim 1, further comprising an output port provided in the housing, wherein the second radiation emitted by the plurality of quantum dots is output through the output port.

15. The radiation source of claim 1, wherein the radiation excitation source is disposed in the housing.

16. A calibration system, comprising:
a quantum dot based radiation source comprising:
a housing having a wall defining a cavity therein;
a plurality of quantum dots disposed on a plurality of substrate panels, the substrate panels disposed on a first portion of an inner surface of the wall;
a radiation excitation source configured to output first radiation to excite the plurality of quantum dots to emit second radiation in a desired wavelength range, the emitted second radiation being output by the quantum dot based radiation source;
a radiation reflective material disposed on a second portion of the inner surface of the wall and not on the first portion of the inner surface of the wall, the first and second portions being mutually exclusive, and the radiation reflective material selected to reflect the second radiation emitted by the plurality of quantum dots; and
an integrating sphere configured to receive the emitted second radiation output by the quantum dot based radiation source.

17. The calibration system of claim 16, wherein the housing is spherical and the first and second portions of the inner surface of the wall of the housing are first and second hemispheres of the wall.

18. A method of calibrating a radiation detector, comprising:
exciting a plurality of quantum dots with a first radiation so that the quantum dots emit a second radiation in a desired wavelength range, the quantum dots being disposed on a plurality of substrate panels disposed on a first portion of an inner surface of a wall of a housing defining a cavity therein;
reflecting and diffusing the second radiation emitted by the plurality of quantum dots with a radiation reflective material disposed only on a second portion of the inner surface of the wall and not on the first portion of the inner surface of the wall, the first and second portions being mutually exclusive;
outputting the second radiation through an output port in the housing;
guiding the second radiation towards the radiation detector; and
calibrating the detector using the second radiation, and establishing a relationship between a signal output by the detector and a photon flux emitted by an object.

19. The method of claim 18, further comprising directing the second radiation emitted by the quantum dots to an integrating sphere and outputting the second radiation through an output port of the integrating sphere.

20. The method of claim 18, wherein a wavelength of the first radiation is shorter than or equal to a wavelength of the second radiation emitted by the quantum dots.

* * * * *